United States Patent
Omran et al.

(10) Patent No.: US 12,350,291 B1
(45) Date of Patent: Jul. 8, 2025

(54) INHIBITION OF CANCER CELL VIABILITY

(71) Applicant: IMAM MOHAMMAD IBN SAUD ISLAMIC UNIVERSITY, Riyadh (SA)

(72) Inventors: Mohamed Khairy Abdel Fattah Omran, Riyadh (SA); Babiker Yagoub Elhadi Abdulkhair, Riyadh (SA)

(73) Assignee: IMAM MOHAMMAD IBN SAUD ISLAMIC UNIVERSITY, Riyadh (SA)

( * ) Notice: Subject to any disclaimer, the term of this patent is extended or adjusted under 35 U.S.C. 154(b) by 0 days.

(21) Appl. No.: 19/064,093

(22) Filed: Feb. 26, 2025

(51) Int. Cl.
*A61K 33/06* (2006.01)
*A61K 9/16* (2006.01)
*A61P 35/00* (2006.01)
*B82Y 5/00* (2011.01)

(52) U.S. Cl.
CPC .............. *A61K 33/06* (2013.01); *A61K 9/16* (2013.01); *A61P 35/00* (2018.01); *B82Y 5/00* (2013.01)

(58) Field of Classification Search
None
See application file for complete search history.

(56) References Cited

FOREIGN PATENT DOCUMENTS

| | | |
|---|---|---|
| CN | 105535972 B | 10/2018 |
| CN | 115108587 A | 9/2022 |
| CN | 111665288 B | 10/2022 |
| IN | 202311022975 | 10/2024 |

OTHER PUBLICATIONS

Arezo Nouri, et al., "Simultaneous linear release of folic acid and doxorubicin from ethyl cellulose/chitosan/g-C3N4/MoS2 core-shell nanofibers and its anticancer properties", Journal of Biomedical Materials Research Part A, vol. 109, Issue 6, Jun. 2021, pp. 903-914 (12 pages).

*Primary Examiner* — Brian J Davis
(74) *Attorney, Agent, or Firm* — Oblon, McClelland, Maier & Neustadt, L.L.P.

(57) ABSTRACT

A method of inhibiting cancer cell viability may include contacting cancer cells and a nanocomposite including graphitic $CaN_4$, $MoO_3$, and $MgAl_2O_4$ in a mass relationship to each other in a range of 5 to 15:2 to 7:75 to 95. The nanocomposite may be contacted with the cancer cells at a concentration range of 25.0 to 500 g/mL, thereby inhibiting the growth of the cancer cells by at least 85%.

20 Claims, 5 Drawing Sheets

INHIBITION OF CANCER CELL VIABILITY

BACKGROUND

Technical Field

The present disclosure is directed towards use of nanohybrids as anti-cancer agents, and more particularly, relates to a method of inhibiting cancer cell viability using a nanocomposite including graphitic $C_3N_4$, $MoO_3$, and $MgAl_2O_4$.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Worldwide, cancer remains a leading cause of death and disability due to a complex pathological process associated with a plurality of cancers. Conventional chemotherapy faces several challenges, including cytotoxicity, low therapeutic indices, low bioavailability, insolubility, high dose requirements, non-specific targeting, and the development of multiple drug resistance. Resistance to cancer treatment arises from various factors such as overexpression of drug efflux transporters, anoxic conditions, and abnormal apoptotic pathways. The aforementioned limitations necessitate the exploration of innovative approaches to improve cancer treatment efficacy and patient outcomes.

Nanomaterials (NMs) have emerged as promising anticancer agents to address the limitations of conventional chemotherapy. The optimization of NMs in terms of size, shape, and surface characteristics enhances targeting efficiency and prolongs circulation time, thereby increasing the targeting potential of anticancer cargos. NMs may enhance therapeutic efficacy through controlled release mechanisms by encapsulating or coupling therapeutic cargos with ligands, providing precise delivery to cancer sites. In cancer treatment, NMs are employed to target cancer cells, the tumor microenvironment, and the immune system through stimuli-responsive targeting or surface modification with targeting ligands such as transferrin, integrins, sugar, folic acid, and antibodies. The aforementioned functionalization may improve tissue targeting, recognition, and internalization, offering a more effective therapeutic approach. The biomedical applications of NMs are extensive, with their ability to transport ligands and therapeutic compounds or to target cancer cells and tissues through passive, active, or physical targeting methods. The above-described advancements aim to achieve stronger inhibitory therapeutic efficacies in the fight against cancer.

Despite certain improved therapeutic methods, the application of nanomaterials in cancer treatment faces several challenges and limitations. Key drawbacks include potential toxicity and long-term biocompatibility concerns, difficulties in large-scale production with consistent quality, and challenges in achieving efficient clearance from the body to avoid accumulation and adverse side effects. Additionally, regulatory and clinical translation hurdles pose significant challenges, requiring extensive preclinical and clinical validation to ensure safety and efficacy. The cost of developing and deploying nanomaterial-based therapies is yet another barrier to widespread clinical adoption. Research in this regard has been conducted by Mandal and colleagues in *J. Drug Delivery Therap.* 2023, 13 (12), 201-223, and by Algethami and colleagues in *Zeitsch. anorg. allgem. Chem.* 2021, 647 (19), 1921-1929, each of which is incorporated by reference herein, but this research leaves issues unresolved.

Accordingly, one object of the present disclosure is to provide a method of inhibiting cancer cell viability, that may circumvent the above listed drawbacks and limitations of the methods known in the art.

SUMMARY

In an exemplary embodiment, a method of inhibiting cancer cell viability is described. The method includes contacting cancer cells and a nanocomposite including graphitic $C_3N_4$, $MoO_3$, and $MgAl_2O_4$ in a mass relationship to each other in a range of 5 to 15:2 to 7:75 to 95. The nanocomposite is in a concentration range of 25.0 micrograms per milliliters (μg/mL) to 500 μg/mL, thereby inhibiting the growth of the cancer cells by at least 85%.

The average pore distribution of the nanocomposite may be unimodal, a Brunauer-Emmett-Teller (BET) specific surface area of the nanocomposite may be in a range of 8 $m^2/g$ to 12 $m^2/g$ (10.1±2.5, 2, 1.5, 1, 0.75, 0.67, 0.5, 0.33, 0.25, 0.125, 0.1, 0.05, or 0.01 $m^2/g$), and/or an average pore diameter of the nanocomposite, according to Barrett-Joyner-Halenda (BJH) measurement method, may be in a range of 5 nanometers (nm) to 15 nm (8.34±1.5, 1, 0.75, 0.67, 0.5, 0.33, 0.25, 0.125, 0.1, 0.05, or 0.01 nm), and/or an average pore volume of the nanocomposite, according to the BJH measurement method, may be in a range of from 0.01 $cm^3/g$ to 0.5 $cm^3/g$ (0.033±0.01, 0.0075, 0.0067, 0.005, 0.0033, 0.0025, 0.00125, 0.001, 0.0005, or 0.0001 $cm^3/g$).

The nanocomposite may have a (311) spinel interplanar spacing in a range of from 0.205 to 0.285 nm, a (411) $MoO_3$ interplanar spacing in a range of from 0.150 to 0.230 nm, a (311) MgO interplanar spacing in a range of from 0.087 to 0.167 nm, and/or a (622) spinel interplanar spacing in a range of from 0.080 to 0.160 nm, according to selected area diffraction (SAED).

The mass relationship of the nanocomposite may be in a range of 9 to 11:4 to 6:84 to 86, where the nanocomposite has a (311) interplanar spacing of 0.245±2% nm, a (411) $MoO_3$ interplanar spacing of 0.19±2% nm, a (511) spinel interplanar spacing of 0.155±2% nm, and a (311) MgO interplanar spacing of 0.127±2% nm, according to SAED, where an X-ray diffraction (XRD) spectrum of the nanocomposite under Cu-filtered Cu-Kα radiation (1.5418 Å) powered at 45 kV and 10 mA may have 2θ peaks of an $MoO_3$ hexagonal phase at 18.7±1°, 28.7±1°, 33.0±1°, 33.8±1°, 36.8±1°, and/or 42.8±1°, an $MgAl_2O_4$ spinel phase at 19.3±1°, 36.8±1°, 44.6±1°, 59.3±1°, and/or 65.01±1°, an MgO cubic phase at 42.8±1°, 62.2±1°, and/or 74.6±1, g-$C_3N_4$-related diffractions at 27.8±1°, 36.8±1°, 44.6±1°, and/or 59.3±1°, and/or no more than 1% relative intensity $Al_2O_3$ is detected in the XRD spectrum.

The cancer cells may be HepG-2 human hepatocellular carcinoma cells and the concentration of the nanocomposite in the contacting may be in a range of 40 μg/mL to 200 μg/mL ($IC_{50}$ against the HepG-2 human hepatocellular carcinoma cells is 62.35±5, 4, 3.33, 2.5, 2, 1.5, 1, 0.75, 0.67, 0.5, 0.33, 0.25, 0.125, 0.1, 0.05, or 0.01 μg/mL). The cancer cells may be MCF-7 human breast carcinoma cancer cells and the concentration of the nanocomposite may be in a range of from 75 μg/mL to 350 μg/mL ($IC_{50}$ against the MCF-7 human breast carcinoma cancer cells is 108.19±15, 10, 7.5, 5, 4, 3.33, 2.5, 2, 1.5, 1, 0.75, 0.67, 0.5, 0.33, 0.25, 0.125, 0.1, 0.05, or 0.01 μg/mL).

The nanocomposite may include no $MoS_2$. The nanocomposite may include no sulfide.

The nanocomposite may include no chitosan and/or no cellulose and/or modified cellulose. The nanocomposite obtained may include no more than 1 wt. % carbonaceous material besides the graphitic carbon nitride.

The nanocomposite may include less than 1 wt. % Co, relative to total nanocomposite weight.

The nanocomposite obtained may include no added Co (only inevitable traces), and/or the method may employ no folic acid and/or no rubicin drug.

The nanocomposite obtained may include no more than 1 wt. % potassium, iron, and/or zinc. The nanocomposite may include no more than 1 wt. % of iron, cobalt, nickel, and/or copper. The nanocomposite may include no more than 0.5 wt. % of elemental metal. The nanocomposite may include no more than 1 wt. % $Ba(OH)_2$.

The method may employ no electrochemiluminescence. The nanocomposite may include no photosensitizer capable of converting oxygen molecules and/or triplet oxygen into singlet oxygen. The nanocomposite may include no more than 0.0001 wt. % methylene blue or protoporphyrin.

The nanocomposite may have a structure including a dispersion of homogeneous spherical metal oxides nanoparticles on a two-dimensional porous structure comprising curled and wrinkled nanosheets and platelets of the $g-C_3N_4$.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
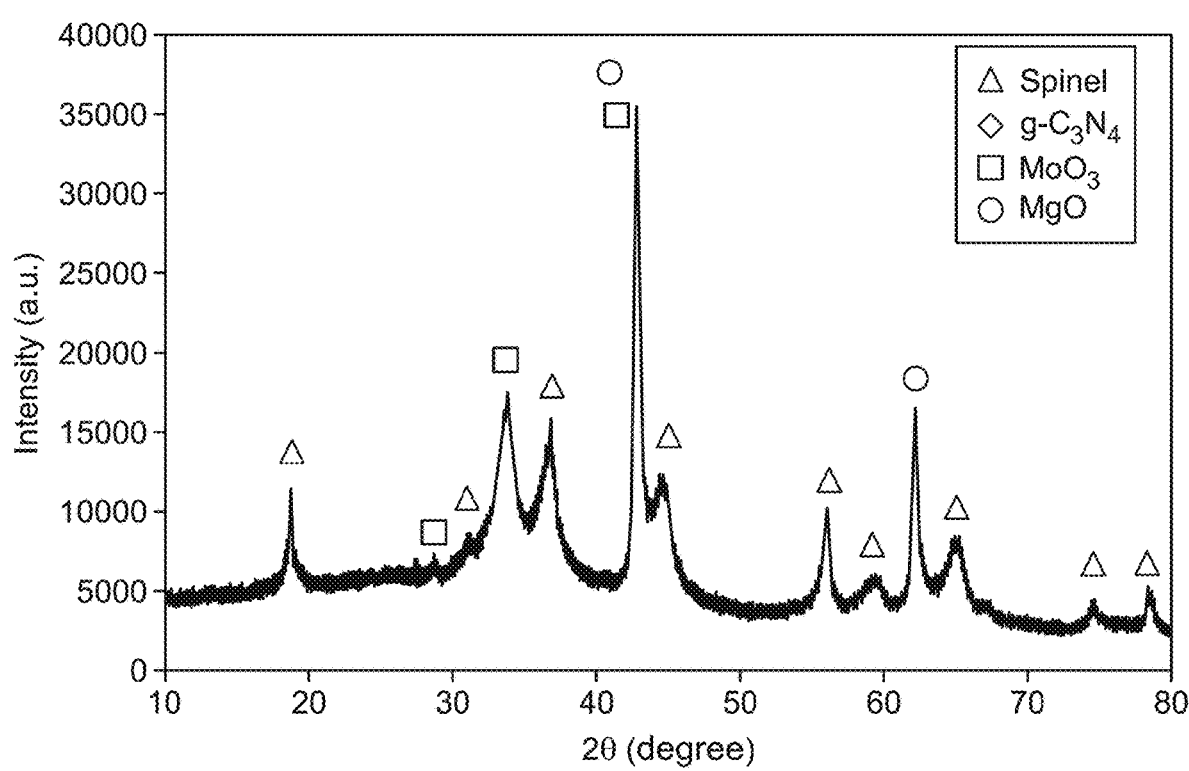
FIG. 1 is a graph depicting X-ray diffraction (XRD) patterns of an inventive 10% $g-C_3N_4@MoO_3/MgAl_2O_4$ nanocomposite.

When describing the present disclosure, the terms used are to be construed in accordance with the following definitions, unless a context dictates otherwise.

Embodiments of the present invention will now be described more fully hereinafter with reference to the accompanying drawings wherever applicable, in that some, but not all, embodiments of the disclosure are shown.

In the drawings, like reference numerals designate identical or corresponding parts throughout the several views. Further, as used herein, the words 'a,' 'an' and the like generally carry a meaning of 'one or more,' unless stated otherwise.

Furthermore, the terms 'approximately,' 'approximate,' 'about,' and similar terms generally refer to ranges that include the identified value within a margin of 20%, 10%, or preferably 5%, and any values therebetween.

As used herein, the term 'cancer' refers to all types of cancer, neoplasm or malignant tumors found in mammals (e.g. humans), including leukemias, lymphomas, carcinomas, and sarcomas. Exemplary cancers that may be treated with a compound or method provided herein include brain cancer, glioma, glioblastoma, neuroblastoma, prostate cancer, colorectal cancer, pancreatic cancer, Medulloblastoma, melanoma, cervical cancer, gastric cancer, ovarian cancer, lung cancer, cancer of the head, Hodgkin's Disease, and Non-Hodgkin's Lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulinoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

As used herein, the term 'cell viability' refers to the proportion of live, healthy cells in a population after being exposed to various conditions or treatments. It is commonly measured to assess the health and functionality of cells in laboratory studies, particularly when testing the effects of drugs, toxins, or other experimental variables. Viable cells can maintain their metabolism, growth, and division processes, while non-viable cells are damaged, dysfunctional, or dead. Cell viability is often assessed using assays that measure metabolic activity, membrane integrity, or other indicators of cellular health.

As used herein, the terms 'treat,' 'treatment,' and 'treating' in the context of the administration of a therapy to a subject in need thereof refer to the reduction or inhibition of the progression and or duration of cancer, the reduction or amelioration of the severity of cancer, and/or the amelioration of one or more symptoms thereof resulting from the administration of one or more therapies. In some embodiments, the subject is a mammalian subject. In one embodiment, the subject is a human. 'Treating' or 'treatment' of a disease includes preventing the disease from occurring in a subject that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). With regard to cancer or hyperplasia, these terms simply mean that the life expectancy of an individual affected with cancer will be increased or that one or more of the symptoms of the disease will be reduced. In specific embodiments, such terms refer to one, two or three or more results following the administration of one, two, three or more therapies: (1) a stabilization, reduction or elimination of the cancer stem cell population; (2) a stabilization, reduction or elimination in the cancer cell population; (3) a stabilization or reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate, (10) a decrease in hospitalization lengths, (11) the size of the tumour is maintained and does not increase or increases by less than 10%, preferably less than 5%, preferably less than 4%, preferably less than 2%, and (12) an increase in the number of patients in remission. In certain embodiments, such terms refer to a stabilization or reduction in cancer stem cell population. In some embodiments, such terms refer to a stabilization or reduction in the growth of cancer cells. In some embodiments, such terms refer to stabilization or reduction in cancer stem cell population and a reduction in the cancer cell population. In some embodiments, such terms refer to a stabilization or reduction in the growth and or formation of a tumour. In some embodiments, such terms refer to the eradication, removal, or control of primary, regional, or metastatic cancer (e.g., the minimization or delay of the spread of cancer). In some embodiments, such terms refer to a reduction in mortality and/or an increase in the survival rate of a patient population. In further embodiments, such terms refer to an increase in the response rate, the durability of response, or the number of patients who respond or are in remission. In some embodiments, such terms refer to a decrease in the hospitalization rate of a patient population and/or a decrease in hospitalization length for a patient population.

As used herein, the term 'pharmaceutical composition' refers to a mixture of the compounds described herein or pharmaceutically acceptable salts, esters, or prodrugs thereof, with other chemical components, such as physiologically acceptable carriers and excipients.

As used herein, the term 'administering' means oral administration, administration as a suppository, topical contact, intravenous, parenteral, intraperitoneal, intramuscular, intralesional, intrathecal, intranasal, or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. The administering may not include administration of any active agent other than the recited active agent.

The administration of the anticancer compound may be selected from intravenous, intraperitoneal, intramuscular, and oral administration.

As used herein, the terms 'anticancer agent' or 'anticancer compound' refer to a molecule (e.g., compound, peptide, protein, nucleic acid, 0103) used to treat cancer through the destruction or inhibition of cancer cells or tissues. Anticancer agents may be selective for certain cancers or certain tissues.

'Anti-cancer agent' and 'anticancer agent' or 'anticancer compound' are used in accordance with their plain ordinary meaning and refers to a composition (e.g. compound, drug, antagonist, inhibitor, modulator) having antineoplastic properties or the ability to inhibit the growth or proliferation of cells. An anti-cancer agent may be chemotherapeutic. An anti-cancer agent may be an agent identified herein having utility in methods of treating cancer. An anti-cancer agent may be an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogs; clotrimazole; collismycin A; collismycin B; combretastatin A4; combretastatin analog; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin;

cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol.TM (i.e. paclitaxel), Taxotere.TM, compounds including the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, Inanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (-)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), immunotherapy (e.g., cellular immunotherapy, antibody therapy, cytokine therapy, combination immunotherapy, etc.), radioimmunotherapy (e.g., anti-CD20 monoclonal antibody conjugated to $^{111}$In, $^{90}$Y, or $^{131}$I, etc.), immune checkpoint inhibitors (e.g., CTLA4 blockade, PD-1 inhibitors, PD-L1 inhibitors, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

As used herein, the term 'nanoparticles (NPs)' refers to particles having a particle size of 1 nanometer (nm) to 500 nm within the scope of the present disclosure.

As used herein, the term 'nanocomposite' is a material that is made by combining a matrix (often a polymer, metal, or ceramic) with NPs or nanomaterials to enhance its properties. The NPs are typically on the scale of nm (1 to 100 nm), and their small size and high surface area can significantly improve the composite material's strength, thermal stability, electrical conductivity, optical properties, and other characteristics.

As used herein, the term 'unimodal' refers to a distribution or pattern that has a single peak or mode. In the context of particle size or material properties, it indicates that the sample consists of particles or components that are primarily of one size or characteristic, rather than varying widely in size or composition.

As used herein, the term 'half maximal inhibitory concentration ($IC_{50}$)' refers to the measure of the potency of a substance in inhibiting a specific biological or biochemical function. $IC_{50}$ is a quantitative measure that indicates how much of a particular inhibitory substance (e.g., drug) is needed to inhibit, in vitro, a given biological process or biological component by 50%. The biological component can be an enzyme, cell, cell receptor or microorganism. $IC_{50}$ values are typically expressed as molar concentration.

As used herein, the term 'pore volume' refers to the total volume of void spaces (pores) within a material that are capable of being filled by a gas or liquid. It is typically expressed in cubic centimeters per gram ($cm^3/g$) and is an important parameter in characterizing the porous structure of materials, such as adsorbents or catalysts.

As used herein, the term 'pore diameter' refers to the average width or size of the pores (void spaces) within a material, typically measured in nm or angstroms (Å). It is a key parameter in characterizing the texture and permeability of porous materials, influencing their adsorption, filtration, or catalytic properties. Pore diameter is often determined using methods such as nitrogen adsorption or mercury intrusion, which provide insights into the material's ability to absorb or interact with molecules of specific sizes.

As used herein, the term 'spinel interplanar spacing' refers to the distance between parallel planes of atoms in the crystal structure of a spinel material. Spinel is a type of mineral with a specific crystalline arrangement, represented by the general formula $AB_2O_4$, where 'A' and 'B' are metal ions. The interplanar spacing is crucial for understanding the material's structural properties and is typically measured using X-ray diffraction (XRD) techniques.

As used herein, the term 'HepG-2 human hepatocellular carcinoma cells' refer to a type of cancer cell line derived from a liver tumour in a human patient.

As used herein, the term 'MCF-7 human breast carcinoma cells' refer to cell line derived from a breast cancer tumour.

As used herein, the term 'antiproliferation agent' refers to a compound or material that inhibits or prevents the proliferation (growth and reproduction) of cells, particularly cancerous or abnormal cells. The antiproliferative effect is achieved through various mechanisms, such as interference with cell cycle progression, induction of apoptosis (programmed cell death), inhibition of DNA/RNA synthesis, or disruption of metabolic pathways essential for cell growth. Antiproliferation agents are generally used in therapeutic applications to target and control the uncontrolled cell division characteristic of cancer and other proliferative disorders.

As used herein, the term 'electrochemiluminescence (ECL)' refers to the emission of light (luminescence) that occurs as a result of an electrochemical reaction. The process typically involves the application of an electric current to a system containing a luminophore or a light-emitting substance. When the electric current triggers the electrochemical reaction, excited species are formed, and as these species return to their ground state, they release energy in the form of visible light.

As used herein, the term 'photosensitizer' refers to the substance that, when exposed to light of a specific wavelength, undergoes a chemical transformation, typically by absorbing the light energy and transferring it to nearby molecules. This process enables the photosensitizer to produce reactive species, such as singlet oxygen or free radicals, which can then induce biological effects, such as the destruction of cancer cells. Photosensitizers are commonly used in photodynamic therapy (PDT), where they help target and treat cancer or other diseases by generating reactive oxygen species (ROS) in response to light exposure, leading to cell damage and death.

A weight percent of a component, unless specifically stated to the contrary, is based on the total weight of the formulation or composition in which the component is included. For example, if a particular element or component in a composition or article is said to have 5 wt. %, it is understood that this percentage is in relation to a total compositional percentage of 100%.

The present disclosure is intended to include all hydration states of a given compound or formula, unless otherwise noted or when heating a material.

In addition, the present disclosure is intended to include all isotopes of atoms occurring in the present compounds and complexes. Isotopes include those atoms having the same atomic number but different mass numbers. By way of general example, and without limitation, isotopes of hydrogen include deuterium and tritium, and isotopes of carbon include $^{13}C$ and $^{14}C$. Isotopes of oxygen include $^{16}O$, $^{17}O$, and $^{18}O$. Isotopically-labeled compounds of the disclosure may generally be prepared by conventional techniques known to those skilled in the art or by processes analogous to those described herein, using an appropriate isotopically-labeled reagent in place of the non-labeled reagent otherwise employed.

Aspects of the present disclosure are directed toward a nanocomposite of graphitic carbon nitride ($g-C_3N_4$), molybdenum oxide ($MoO_3$), and magnesium aluminate ($MgAl_2O_4$) ($g-C_3N_4@MoO_3/MgAl_2O_4$). The nanocomposite is designed as an anticancer agent, demonstrating effective cytotoxicity against human breast carcinoma (MCF-7) and hepatocellular carcinoma (HepG-2) cell lines.

A nanocomposite ($g-C_3N_4@MoO_3/MgAl_2O_4$) including $g-C_3N_4$, $MoO_3$, and $MgAl_2O_4$ is described. The nanocomposite includes coating of the $g-C_3N_4$ $MoO_3$, and $MgAl_2O_4$. The graphitic $C_3N_4$, $MoO_3$, and $MgAl_2O_4$ are present in the nanocomposite in a mass relationship to each other in a range of from 5 to 15:2 to 7:75 to 95 (±5, 4, 3.33, 2.5, 2, 1.5, 1, 0.75, 0.67, 0.5, 0.33, 0.25, 0.125, 0.1, 0.05, or 0.01), preferably 7 to 13:3 to 6:80 to 90, preferably 9 to 11:4 to 5:84 to 86, and yet more preferably 10:5:85, while these values may vary, e.g., by ±4, 3.33, 2.5, 2, 1.5, 1, 0.75, 0.67, 0.5, 0.33, 0.25, 0.125, 0.1, 0.05, or 0.01.

The nanocomposite obtained may include no molybdenum sulfide ($MoS_2$), or no added $MoS_2$, or, e.g., no more than 5, 4, 3, 2.5, 2, 1, 0.5, 0.1, 0.01, 0.001, 0.0001, or 0.00001 wt. % $MoS_2$, relative to the total nanocomposite weight. The nanocomposite may include no sulfide, or no added sulfide (i.e., analog to ether), or, e.g., no more than 5, 4, 3, 2.5, 2, 1, 0.5, 0.1, 0.01, 0.001, 0.0001, or 0.00001 wt. % sulfide, relative to the total nanocomposite weight. The nanocomposite may include less than 1 wt. % Co, preferably less than 0.9 wt. % Co, preferably less than 0.8 wt. % Co, preferably less than 0.7 wt. % Co, preferably less than 0.6 wt. % Co, preferably less than 0.5 wt. % Co, preferably less than 0.4 wt. % Co, preferably less than 0.3 wt. % Co, preferably less than 0.2 wt. % Co, preferably less than 0.1 wt. % Co, preferably less than 0.05 wt. % Co, and preferably less than 0.01 wt. % Co. The nanocomposite may contain no added Co (only inevitable traces) or no more than 5, 4, 3, 2.5, 2, 1, 0.5, 0.1, 0.01, 0.001, 0.0001, or 0.00001 wt. % Co, relative to total nanocomposite weight. The exclusion of $MoS_2$ or sulfide, and the minimization of Co content in the nanocomposite may ensure the preservation of its desired catalytic properties, stability, and reactivity. The absence of $MoS_2$ or sulfide prevents undesirable side reactions, while limiting the Co content to less than 1 wt. % prevents interference and potential toxicity, thereby enhancing the performance and applicability of the nanocomposite.

The nanocomposite may include no (added) chitosan, cellulose, modified cellulose, and/or folic acid, or no more than 5, 4, 3, 2.5, 2, 1, 0.5, 0.1, 0.01, 0.001, 0.0001, or 0.00001 wt. %, individually or in any combination, of chitosan, cellulose, modified cellulose, and/or folic acid, relative to total carbonaceous material weight. The nanocomposite may include no folic acid and/or rubicin drug, or no more than 5, 4, 3, 2.5, 2, 1, 0.5, 0.1, 0.01, 0.001, 0.0001, or 0.00001 wt. % of folic acid and/or rubicin drug.

The nanocomposite may include no more than 1 wt. % potassium, or less than 0.9 wt. %, 0.8 wt. %, 0.7 wt. %, 0.6 wt. %, 0.5 wt. %, 0.4 wt. %, 0.3 wt. %, 0.2 wt. %, 0.1 wt. %, 0.05 wt. %, or less than 0.01 wt. % potassium.

The nanocomposite may include no more than 1 wt. % iron, preferably less than 0.9 wt. % iron, preferably less than 0.8 wt. % iron, preferably less than 0.7 wt. % iron, preferably less than 0.6 wt. % iron, preferably less than 0.5 wt. % iron, preferably less than 0.4 wt. % iron, preferably less than 0.3 wt. % iron, preferably less than 0.2 wt. % iron, preferably less than 0.1 wt. % iron, preferably less than 0.05 wt. % iron, and preferably less than 0.01 wt. % iron.

The nanocomposite may include no more than 1 wt. % zinc, preferably less than 0.9 wt. % zinc, preferably less than 0.8 wt. % zinc, preferably less than 0.7 wt. % zinc, preferably less than 0.6 wt. % zinc, preferably less than 0.5 wt. % zinc, preferably less than 0.4 wt. % zinc, preferably less than 0.3 wt. % zinc, preferably less than 0.2 wt. % zinc, preferably less than 0.1 wt. % zinc, preferably less than 0.05 wt. % zinc, and preferably less than 0.01 wt. % zinc.

The nanocomposite may include no more than 1 wt. %, preferably less than 0.9 wt. %, preferably less than 0.8 wt. %, preferably less than 0.7 wt. %, preferably less than 0.6 wt. %, preferably less than 0.5 wt. %, preferably less than 0.4 wt. %, preferably less than 0.3 wt. %, preferably less than 0.2 wt. %, preferably less than 0.1 wt. %, preferably less than 0.05 wt. %, and preferably less than 0.01 wt. % of iron, cobalt, nickel, and/or copper.

The nanocomposite obtained may include no more than 1 wt. % carbonaceous material, or less than 0.9, 0.8, 0.7, 0.6, 0.5, 0.4, 0.3, 0.2, 0.1, 0.05, or 0.01 wt. % of carbonaceous material besides the graphitic carbon nitride.

The method of the present disclosure may employ no electrochemiluminescence. The nanocomposite may include no photosensitizer capable of converting oxygen molecules and/or triplet oxygen into singlet oxygen. The nanocomposite may include no more than 0.5, 0.1, 0.01, 0.001, 0.0001, or 0.00001 wt. % of elemental metal. The nanocomposite may include no more than 0.0001 wt. % methylene blue or protoporphyrin. The nanocomposite may include no more than 1, 0.75, 0.67, 0.5, 0.33, 0.25, 0.1, 0.01, 0.001, 0.0001, or 0.00001 wt. % barium hydroxide ($Ba(OH)_2$).

The purpose of these specific limitations and exclusions in the nanocomposite embodiment is to define its unique composition, ensuring that it maintains distinct properties suitable for anticancer applications while avoiding interference from other materials or compounds. These exclusions ensure that the nanocomposite remains free of common additives, such as chitosan, cellulose, folic acid, rubicin, and photosensitizers, which may affect its mechanism of action or performance. The restrictions on metal content (e.g., potassium, iron, zinc, copper) and elemental metals (such as $Ba(OH)_2$, methylene blue, or protoporphyrin) ensure that the nanocomposite is not contaminated with materials that may lead to undesired side effects or alter its anticancer efficacy. The specific structure of the nanocomposite, with homogeneous spherical metal oxide nanoparticles dispersed on the porous g-$C_3N_4$, is designed to enhance its anticancer properties without relying on electrochemiluminescence or photosensitization, ensuring a targeted mechanism for inhibiting cancer cell viability. These limitations define a well-controlled, pure nanocomposite for use in cancer treatment.

The nanocomposite may be porous. A porous material is the one that forms a porous bulk solid. Pores may be micropores, mesopores, macropores, and/or a combination thereof. The pores exist in the bulk material, not necessarily in the molecular structure of the material. The term 'microporous' means that nanocomposite have pores with an average pore width (i.e. diameter) of less than 2 nm, e.g., in a range with an upper limit of 2, 1, 0.9, 0.75, 0.5, 0.25, 0.1, 0.05, or 0.01 nm, and/or a lower limit of 0.00001, 0.0001, 0.001, 0.01, 0.1, 0.25, 0.5, 0.75, or 1 nm. The term 'mesoporous' means the pores of the nanocomposite have an average pore width of 2 to 50 nm, though this may include subranges within this general range, e.g., a minimum diameter of 2, 3, 5, 10, 15, 20, 25, or 35 m, and/or a maximum diameter of 50, 45, 40, 35, 30, 25, 20, 15, or 10 nm. The term 'macroporous' means the pores of nanocomposite have an average pore width larger than 50 nm, e.g., at least 55, 75, 100, 250, 500, 750, or 1000 nm. Pore size may be determined by methods including, but not limited to, gas adsorption (e.g. $N_2$ adsorption), mercury intrusion porosimetry, and imaging techniques such as scanning electron microscopy (SEM), and X-ray computed tomography (XRCT).

A Brunauer-Emmett-Teller (BET) specific surface area of the nanocomposite may be in a range of from 8 to 12 square meters per gram ($m^2/g$), preferably 9 to 11 $m^2/g$, and preferably 10 to 10.5 $m^2/g$. The surface area on the nanocomposite may be 10.1±2.5, 2, 1.5, 1, 0.75, 0.67, 0.5, 0.33, 0.25, 0.125, 0.1, 0.05, or 0.01 $m^2/g$. The BET hypothesis is the foundation for a significant analysis method for determining the specific surface area of a material. It attempts to explain the physical adsorption of gas molecules on a solid surface. Specific surface area is a property of solids, which is the total surface area of a material per unit of mass, solid or bulk volume, or cross-sectional area. In some embodiments, pore diameter, pore volume, and BET surface area are measured by gas adsorption analysis, preferably $N_2$ adsorption analysis (e.g., $N_2$ adsorption isotherms).

An average pore diameter of the nanocomposite, according to Barrett-Joyner-Halenda (BJH) measurement method, may be in a range of from 5 to 15 nm, preferably 6 to 14 nm, preferably 7 to 13 nm, preferably 8 to 12 nm, and preferably 9 to 11 nm. The nanocomposite may have an average pore diameter of 8.34±2.5, 2, 1.5, 1, 0.5, 0.1, 0.05, 0.025, or 0.01 nm.

An average pore volume of the nanocomposite, according to the BJH measurement method, may be in a range of from 0.01 to 0.5 cm$^3$/g, preferably 0.02 to 0.4 cm$^3$/g, preferably 0.03 to 0.3 cm$^3$/g, preferably 0.04 to 0.2 cm$^3$/g, and preferably 0.05 to 0.1 cm$^3$/g. The average pore volume of the nanocomposite may be 0.033 cm$^3$/g±0.1, 0.05, 0.025, or 0.01 cm$^3$/g.

In some embodiments, an average pore distribution of the nanocomposite may include, but is not limited to, crystalline average pore distribution, bimodal, trimodal, multimodal, narrow, broad and gaussian. The average pore distribution of the nanocomposite may be unimodal. In a preferred embodiment, the average pore distribution of nanocomposite is unimodal, indicating a single dominant pore size within the material. This unimodal distribution suggests that the nanocomposites possess a relatively narrow pore size range, which can result in more uniform pore structures, enhancing specific properties such as adsorption capacity, catalytic activity, or surface reactivity.

The nanocomposite may have a (311) spinel interplanar spacing in a range of from 0.205 to 0.285 nm, preferably 0.215 to 0.275 nm, preferably 0.225 to 0.265 nm, and preferably 0.235 to 0.255 nm; (411) $MoO_3$ interplanar spacing in a range of from 0.150 to 0.230 nm, preferably 0.160 to 0.220 nm, preferably 0.170 to 0.210 nm, and preferably 0.180 to 0.200 nm; (511) spinel interplanar spacing in a range of from 0.115 to 0.195 nm, preferably 0.125 to 0.185 nm, preferably 0.135 to 0.175 nm, and preferably 0.145 to 0.165 nm; (311) MgO interplanar spacing in a range of from 0.087 to 0.167 nm, preferably 0.097 to 0.157 nm, preferably 0.107 to 0.147 nm, and preferably 0.117 to 0.137 nm; and/or (622) spinel interplanar spacing in a range of from 0.080 to 0.160 nm, preferably 0.090 to 0.150 nm, preferably 0.100 to 0.140 nm, and preferably 0.110 to 0.130 nm, according to SAED.

The nanocomposite may have a (311) spinel interplanar spacing of 0.245±2, 1, 0.5, or 0.1% nm, (411) $MoO_3$ interplanar spacing of 0.19±2% nm, (511) spinel interplanar spacing of 0.155±2, 1, 0.5, or 0.1% nm, (311) MgO interplanar spacing of 0.127±2, 1, 0.5, or 0.1% nm, and/or (622) spinel interplanar spacing of 0.12±2, 1, 0.5, or 0.1% nm, according to selected area diffraction (SAED).

The mass relationship of the nanocomposite may be in a range of from 9 to 11:4 to 6:84 to 86, and preferably 9.5 to 10.5:4.5 to 5.5:84.5 to 85.5. The mass relationship of the nanocomposite may be 10:5:85. An XRD spectrum of the nanocomposite under Cu-filtered Cu Kα radiation (1.5418 Å) powered at 45 kilovolt (kV) and 10 milliampere (mA) has 20 peaks of a $MoO_3$ hexagonal phase at 18.7±1°, 28.7±1°, 33.0±1°, 33.8±1°, 36.8±1°, and/or 42.8±1°, an $MgAl_2O_4$ spinel phase at 19.3±1°, 36.8±1°, 44.6±1°, 59.3±1°, and/or 65.0±1°; an MgO cubic phase at 42.8±1°, 62.2±1°, and/or 74.6±1°; and g-$C_3N_4$-related diffractions at 27.8±1°, 36.8±1°, 44.6±1°, and/or 59.3±1°. No more than 1% relative intensity $Al_2O_3$, e.g., less than 0.5, 0.25, 0.1, or 0.1%, may be detected in the XRD spectrum. The minimal presence of $Al_2O_3$ (less than 1%) in the nanocomposite is critical to maintaining its enhanced catalytic properties, high surface reactivity, and efficient adsorption. This ensures desired performance in environmental remediation, energy production, and biomedical applications, free from interference by less reactive $Al_2O_3$ phases.

The $MoO_3$ in the nanocomposite may have a hexagonal crystal structure, e.g., at least 75, 80, 85, 90, 91, 92, 92.5, 93, 94, 95, 96, 97, 97.5, 98, 99, 99.1, 99.5, or 99.9% of the total phases, or exclusively. The $MoO_3$ may exist in other crystal phases including cubic, monoclinic, tetragonal, rhombohedral, and orthorhombic phases, or any of these may be no more than 15, 10, 7.5, 5, 4, 3, 2, 1, 0.5, or 0.1% of the total phases. MgO may have a cubic phase, e.g., at least 75, 80, 85, 90, 91, 92, 92.5, 93, 94, 95, 96, 97, 97.5, 98, 99, 99.1, 99.5, or 99.9% of the total phases. MgO may exist in other crystal phases including hexagonal, monoclinic, tetragonal, rhombohedral, and orthorhombic phases, or any of these may be no more than 15, 10, 7.5, 5, 4, 3, 2, 1, 0.5, or 0.1% of the total phases.

$MgAl_2O_4$ may have a spinel phase, for example at least 95, 97.5, 99, 99.9%, or exclusively. The spinel phase is a mixed oxide with the general formula $AB_2O_4$, including one divalent cation ($A^{2+}$) and two trivalent cations ($B^{3+}$). The unit cell consists of a face-centered cubic arrangement of oxygen ions, containing 32 $O^{2-}$ ions, with 64 tetrahedral and 32 octahedral sites occupied by $A^{2+}$ and $B^{3+}$ cations. When one half of the octahedral interstices are occupied by $B^{3+}$ cations and one-eighth of the tetrahedral sites are occupied by $A^{2+}$ cations, the spinel phase is termed "normal." Conversely, when tetrahedral sites are occupied by half of the $B^{3+}$ and octahedral sites by the other half along with $A^{2+}$, the spinel phase is termed "inverse."

The spinel phase with the chemical formula $MgAl_2O_4$ is a mineral type of this oxide family. $MgAl_2O_4$ has been widely used in various applications, such as in metallurgical, electrochemical, radio-technical, and chemical industrial fields owing to its high thermal stability (melting point at 2135 degrees Celsius (° C.), high hardness (16 gigapascal (GPa)), high mechanical resistance, high resistance against chemical attack, wide band gap energy, high electrical resistivity, relatively low thermal expansion coefficient (9.10$^{-6}$ 1/° C.) between 3° and 1400° C., low dielectric constant, low density (3.58 gram per cubic centimeter (g/cm$^3$)), high thermal shock resistance, hydrophobicity, and low surface acidity. A method of inhibiting the cancer cell viability may include contacting cancer cells and the nanocomposite. The nanocomposite of the present disclosure may then be administered orally, systemically, parenterally, by inhalation spray, rectally, or topically in dosage unit formulations containing conventional non-toxic pharmaceutically acceptable carriers, adjuvants, and vehicles as desired.

The nanocomposite is contacted with the cancer cells at a concentration in a range of from 25.0 to 500 µg/mL, preferably 50.0 to 475 µg/mL, preferably 75.0 to 450 µg/mL, preferably 100.0 to 425 µg/mL, preferably 125.0 to 400 µg/mL, preferably 150.0 to 375 µg/mL, preferably 175.0 to 350 µg/mL, preferably 200.0 to 325 µg/mL, preferably 225.0 to 300 µg/mL, preferably 250.0 to 275 µg/mL thereby inhibiting the growth of the cancer cells by at least 85%, preferably 86%, preferably 87%, preferably 88%, preferably 89%, preferably 90%, preferably 91%, and preferably 92%. The $IC_{50}$ may be 108.19±3, 2.5, 2, 1.5, 1, 0.5, 0.25, or 0.1 µg/mL, and the maximum dose (500 µg/mL) showed a 90.3% inhibition of the MCF-7 human breast carcinoma cancer cells. The $IC_{50}$ may be 62.35±3, 2.5, 2, 1.5, 1, 0.5, 0.25, or 0.1 µg/mL, and the maximum dose (500 µg/mL) showed a 94.1% inhibition of the HepG-2 human hepatocellular carcinoma cancer cells.

The method of administration of the nanocomposite may be oral. The nanocomposite may be administered by injection, such as, for example, through a perituomoral injection. Topical administration can also involve the use of transdermal administration, such as transdermal patches or iontophoresis devices. The term parenteral, as used herein, includes intravesical, intradermal, transdermal, subcutaneous, intramuscular, intralesional, intracranial, intrapulmonary, intracardial, intrasternal, and sublingual injections, or infusion techniques.

Injectable preparations, for example, sterile injectable aqueous or oleaginous suspensions, can be formulated according to the known art using suitable dispersing or wetting agents and suspending agents. The sterile injectable preparation can also be a sterile injectable solution or suspension in a nontoxic, parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose, any fixed oil can be employed, including synthetic mono- or diglycerides. In addition, fatty acids such as oleic acid find use in the preparation of injectables. Dimethyl acetamide, surfactants including ionic and non-ionic detergents, and polyethylene glycols can be used. Mixtures of solvents and wetting agents, such as those discussed above, are also useful. Suppositories for rectal administration of the compound or an analogue or derivative thereof can be prepared by mixing the steroid or an analogue or derivative thereof with a suitable non-irritating excipient such as cocoa butter, synthetic mono- di- or triglycerides, fatty acids, and polyethylene glycols that are solid at ordinary temperatures but liquid at the rectal temperature and will therefore melt in the rectum and release the drug.

Solid dosage forms for oral administration can include capsules, tablets, pills, powders, and granules. In such solid dosage forms, the compounds of this disclosure are ordinarily combined with one or more adjuvants appropriate to the indicated route of administration. If administered a contemplated steroid or an analogue or derivative thereof can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation, as can be provided in a dispersion of the active compound in hydroxypropyl methylcellulose. In the case of capsules, tablets, and pills, the dosage forms can also include buffering agents such as sodium citrate, magnesium or calcium carbonate, or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. A contemplated steroid or an analog or derivative thereof of the present disclosure can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also include adjuvants, such as wetting agents, emulsifying and suspending, agents, and sweetening, flavoring, and perfuming agents.

The cancer cells may be MCF-7 human breast carcinoma cancer cells, and the concentration of the nanocomposite that is contacted with the cancer cells may be in a range of from 75 to 350 micrograms per liter (µg/mL), preferably 85 to 340 µg/mL, preferably 95 to 330 µg/mL, preferably 105 to 320 µg/mL, preferably 115 to 310 µg/mL, preferably 125 to 300 µg/mL, preferably 135 to 290 µg/mL, preferably 145 to 280 µg/mL, preferably 155 to 270 µg/mL, preferably 165 to 260 µg/mL, preferably 175 to 250 µg/mL, preferably 185 to 240 µg/mL, preferably 195 to 230 µg/mL, preferably 205 to 220 µg/mL, and preferably 215 to 210 µg/mL. The $IC_{50}$ against the MCF-7 human breast carcinoma cancer cells may be 108.19±3, 2.5, 2, 1.5, 1, 0.5, 0.25, or 0.1 µg/mL. The cancer cells may be HepG-2 human hepatocellular carcinoma cells and the concentration of the nanocomposite at the time of contacting the cancer cells may be in a range of from 40 to 200 µg/mL, preferably 50 to 190 µg/mL, preferably 60 to 180 µg/mL, preferably 70 to 170 µg/mL, preferably 80 to 160 µg/mL, preferably 90 to 150 µg/mL, preferably 100 to 140 µg/mL, preferably 110 to 130 µg/mL. The $IC_{50}$ against the HepG-2 human hepatocellular carcinoma cells may be 62.35±3, 2.5, 2, 1.5, 1, 0.5, 0.25, or 0.1 µg/mL The morphology of $g-C_3N_4$ may be nanowires, nanospheres, nanocrystals, nanorectangles, nanotriangles, nanopentagons, nanohexagons, nanoprisms, nanodisks, nanocubes, nanoribbons, nanoblocks, nanotoroids, nanodiscs, nanobarrels, nanogranules, nanowhiskers, nanoflakes, nanofoils, nanopowders, nanoboxes, nanobeads, nanobelts, nanourchins, nanoflowers, nanostars, tetrapods, etc., and mixtures thereof. The $g-C_3N_4$ in the nanocomposite may consist essentially of sheet morphologies, "consisting essentially of" here meaning that the anticancer activity of the nanocomposite is affected by no more than 2.5% in inhibiting cancer cell growth. The nanocomposite may have a structure including a dispersion of homogeneous spherical metal oxides nanoparticles on a two-dimensional porous structure including curled and wrinkled nanosheets and platelets of the $g-C_3N_4$.

The methods for inhibiting cancer and other proliferative disorders described herein may inhibit, remove, eradicate, reduce, regress, diminish, arrest, or stabilize a cancerous tumor, including at least one of the tumor growth, tumor cell viability, tumor cell division, and proliferation, tumor metabolism, blood flow to the tumor and metastasis of the tumor. After contacting cancer cells, the size of a tumor, whether by volume, weight, or diameter, may be reduced by at least 5, 10, 15, 20, 25, 30, 40, 50, 60, 70, 75, 80, 85, 90, 92.5, 95, 97.5, 98, 99, 99.1, 99.5, or 99.9%, relative to the tumor size before treatment. After contacting cancer cells, the size of a tumor may not reduce but may be maintained the same as the tumor size before treatment. Methods of assessing tumor size include, but are not limited to, computed tomography scan (CT scan), magnetic resonance imaging (MRI), dynamic contrast-enhanced magnetic resonance imaging (DCE-MRI), and positron emission tomography scan (PET scan).

The dosage and inhibition duration are dependent on factors such as the bioavailability of a drug, administration mode, toxicity of a drug, gender, age, lifestyle, body weight, the use of other drugs and dietary supplements, cancer stage, tolerance, and resistance of the body to the administered drug, etc., then determined and adjusted accordingly. The nanocomposite may be administered in a single dose or multiple individual divided doses. In some embodiments, the interval of time between the administration of the nanocomposite and the administration of one or more additional therapies may be about 1 to 5 minutes (min), 1 to 30 min, 30 min to 60 min, 1 hour, 1 to 2 hours, 2 to 6 hours, 2 to 12 hours, 12 to 24 hours, 1 to 2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11 to 15 weeks, 15 to 20 weeks, 20 to 30 weeks, 30 to 40 weeks, 40 to 50 weeks, 1 month, 2 months, 3 months, 4 months 5 months, 6 months, 7 months, 8 months, 9 months, 10 months, 11 months, 12 months, 1 year, 2 years, or any period in between. In certain embodiments, the nanocomposite and one or more additional therapies are administered less than 1 day, 1 week, 2 weeks, 3 weeks, 4 weeks, one month, 2 months, 3 months, 6 months, 1 year, 2 years, or 5 years apart.

The nanocomposite or a pharmaceutical composition thereof may be used in combination with one or more other antineoplastic or chemotherapeutic agents. A non-limiting list of examples of chemotherapeutic agents are aflibercept, asparaginase, bleomycin, busulfan, carmustine, chlorambucil, cladribine, cyclophosphamide, cytarabine, dacarbazine, daunorubicin, doxorubicin, etoposide, fludarabine, gemcitabine, hydroxyurea, idarubicin, ifosamide, irinotecan, lomustine, mechclorethamine, melphalan, mercaptopurine, methotrexate, mitomycin, mitoxantrone, pentostatin, procarbazine, 6-thioguanine, topotecan, vinblastine, vincristine, retinoic acid, oxaliplatin, cis-platin, carboplatin, 5-FU (5-fluorouracil), teniposide, amasacrine, docetaxel, paclitaxel, vinorelbine, bortezomib, clofarabine, capecitabine, actinomycin D, epirubicine, vindesine, methotrexate, tioguanine (6-thioguaniue), tipifarnib. Examples of antineoplastic agents which are protein kinase inhibitors include imatinib, erlotinib, sorafenib, sunitinib, dasatinib, nilotinib, lapatinib, gefitinib, temsirolimus, everolimus, rapamycin, bosutinib, pazopanib, axitinib, neratinib, vatalanib, pazopanib, midostaurin, and enzastaurin. Examples for antineoplastic agents which are antibodies include trastuzumab, cetuximab, panitumumab, rituximab, bevacizumab, mapatumumab, conatumumab, lexatumumab and the like.

EXAMPLES

The following examples demonstrate a method of inhibiting cancer cell viability by utilizing a nanocomposite. The examples are provided solely for illustration and are not to be construed as limitations of the present disclosure, as many variations thereof are possible without departing from the spirit and scope of the present disclosure.

Example 1: Fabrication of g-$C_3N_4$@$MoO_3$/ $MgAl_2O_4$ (10:5:85, Wt. %) Nanocomposite According to the present disclosure, magnesium nitrate, and aluminum nitrate were added together in one beaker with ammonium molybdate (($NH_4$)$_2$$MoO_4$), in a predetermined amount, here stoichiometric, to produce a 10% $MoO_3$@$MgAl_2O_4$ nanocomposite. Further, about 10 grams (g) of methanol as a fuel was added to the beaker, followed by 30 milliliters (mL) of distilled water. The beaker was heated till a clear solution was obtained, and heated further till dryness. The obtained product was ground in a mortar, transferred to a 150 mL porcelain dish, and calcined at 700° C. for 3.0 hours. Furthermore, the 10% $MoO_3$@$MgAl_2O_4$ product was cooled down to room temperature and weighed, ground with urea in an amount suitable (depending upon the reaction conditions, this may be 5, 10, 15, 20, 25, 33, 50, 100, 150, 250, 500, or 1000 parts by weight of urea to 100 parts by weight of 10% $MoO_3$/$MgAl_2O_4$, and optionally no more than 100,000, 50,000, 25,000, 10,000, 5,000, 1,000, 750, 500, 400, 333, 250, 125, 100, 75, 50, or 25 parts by weight urea to 100 parts) to produce g-$C_3N_4$@$MoO_3$/ $MgAl_2O_4$ (10:5:85, wt. %) nanocomposite. The quadruple mixture was returned and heated to 600° C. for 60 minutes in a covered porcelain crucible, and subsequently, the g-$C_3N_4$@$MoO_3$/$MgAl_2O_4$ (10:5:85, wt. %) nanocomposite was collected.

Example 2: Characterization

X-ray diffraction XRD was used to identify the crystalline states in each specimen, employing the JDX-8030 X-ray, JEOL, made in Japan. Cu-filtered Cu-Kα radiation (1.5418 Å) powered at 45 kV and 10 mA was used to run the patterns. The specimens were tested at ambient temperatures in a range of 2θ=5° to 80°. The surface morphologies of the obtained samples were analyzed using images of transmission electron microscopy (TEM), selected area electron diffraction (SAED), and high-resolution transmission electron microscopy (HRTEM), obtained by a Tecnai-G20 (USA) transmission electron microscope with a 200 kV speed voltage.

Results and Discussion

As mentioned above, XRD was used to examine the crystallinity and phase identification of the g-$C_3N_4$@$MoO_3$/ $MgAl_2O_4$ catalyst, the results are depicted in FIG. 1. The high crystalline nature of the nanocomposite was shown by strong peaks, as shown in FIG. 1. The phases of $MoO_3$, MgO, $MgAl_2O_4$, and g-$C_3N_4$ were identified by analyzing the diffraction patterns in comparison with the normal JCPDS cards. The hexagonal phase of $MoO_3$ is represented by diffractions at 2θ values of 18.7°, 28.7°, 33.0°, 33.8°, 36.8°, and 42.8° (JCPDS No. 00-021-0569). At 2θ values of 42.8°, 62.2°, and 74.6°, the cubic phase of MgO (JCPDS card, No. 45-0946) was detected. At 2θ values of 19.3°, 36.8°, 44.6°, 59.3°, and 65.01°. $MgAl_2O_4$ spinel was found. The cubic phase of $MgAl_2O_4$ spinel is identified by the aforementioned diffractions (JCPDS card, No. 21-1152). It was previously reported that MgO was present together with the $MgAl_2O_4$ spinel phase. The g-$C_3N_4$-related diffractions were detected at 27.8°, 36.8°, 44.6°, and 59.3°. Subsequently, the production of g-$C_3N_4$@$MoO_3$/$MgAl_2O_4$ was shown by the absence of additional phases (such as $Al_2O_3$).

Figure 2A:
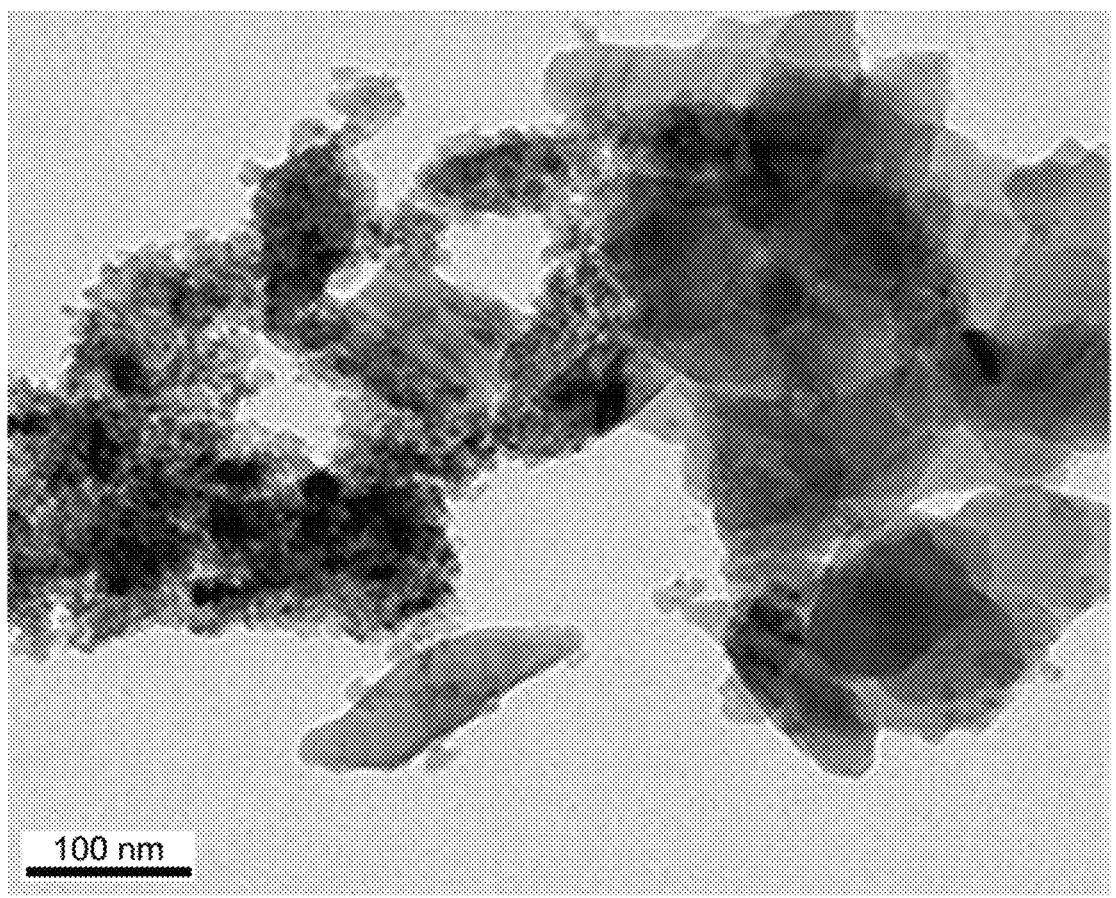
FIG. 2A is a transmission electron microscopy (TEM) image of an inventive 10% $g-C_3N_4@MoO_3/MgAl_2O_4$ nanocomposite.
Figure 2B:
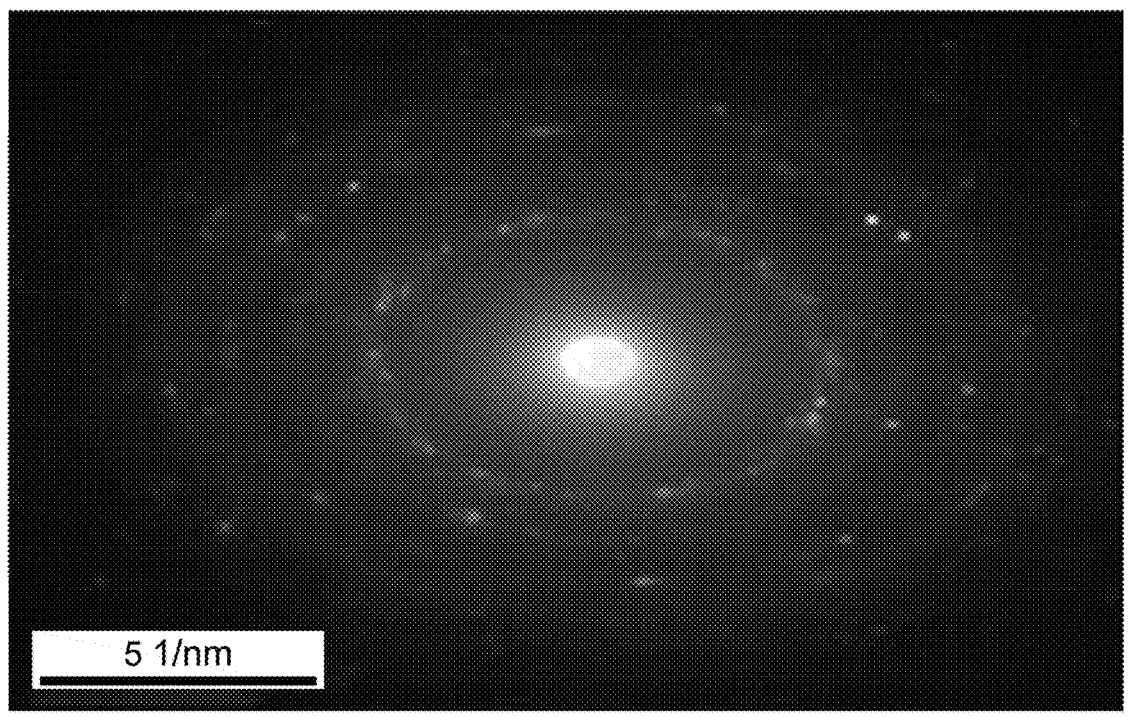
FIG. 2B is a selected area electron diffraction (SAED) pattern of an inventive 10% $g-C_3N_4@MoO_3/MgAl_2O_4$ nanocomposite.
Figure 2C:
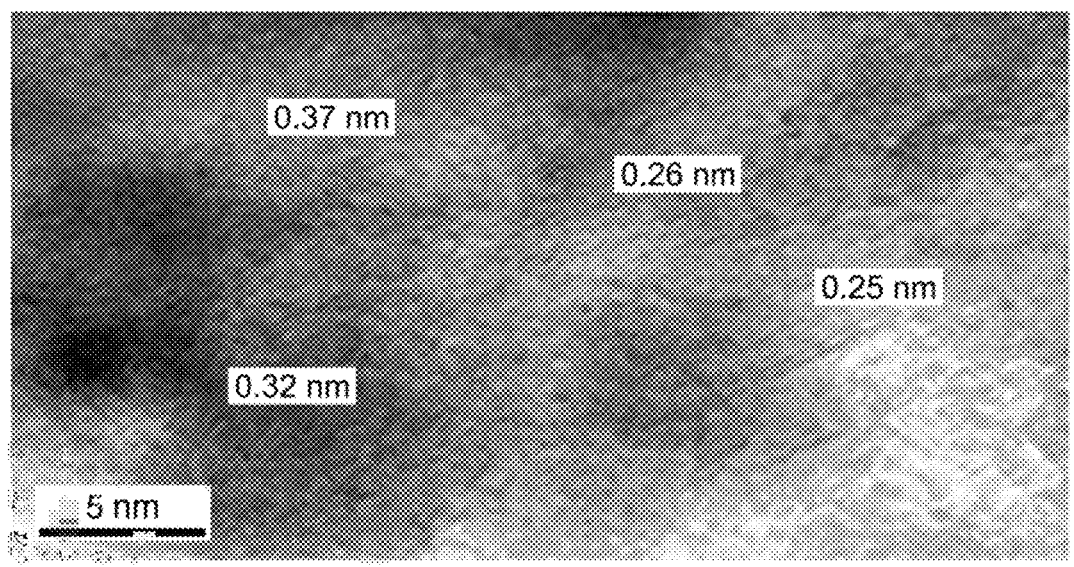
FIG. 2C is a high-resolution transmission electron microscopy (HRTEM) image of an inventive 10% $g-C_3N_4@MoO_3/MgAl_2O_4$ nanocomposite.
Figure 2D:
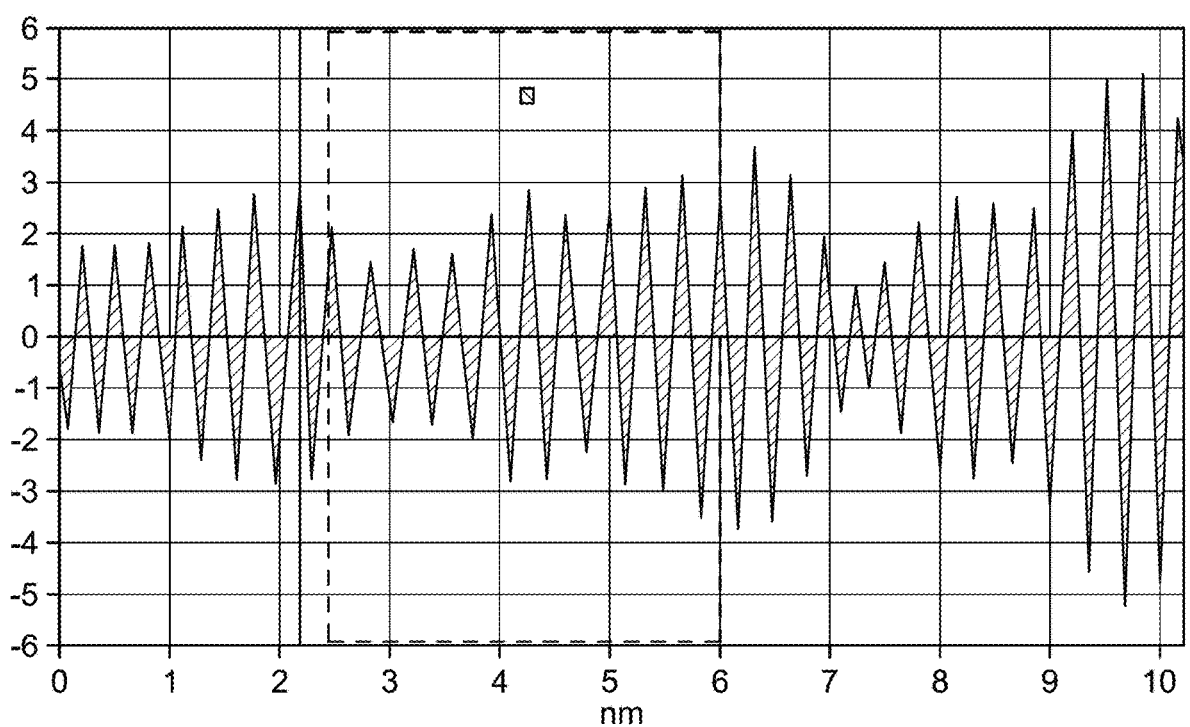
FIG. 2D is a graph depicting fast Fourier transform (FFT) spectra image of an inventive 10% $g-C_3N_4@MoO_3/MgAl_2O_4$ nanocomposite.
Figure 2E:
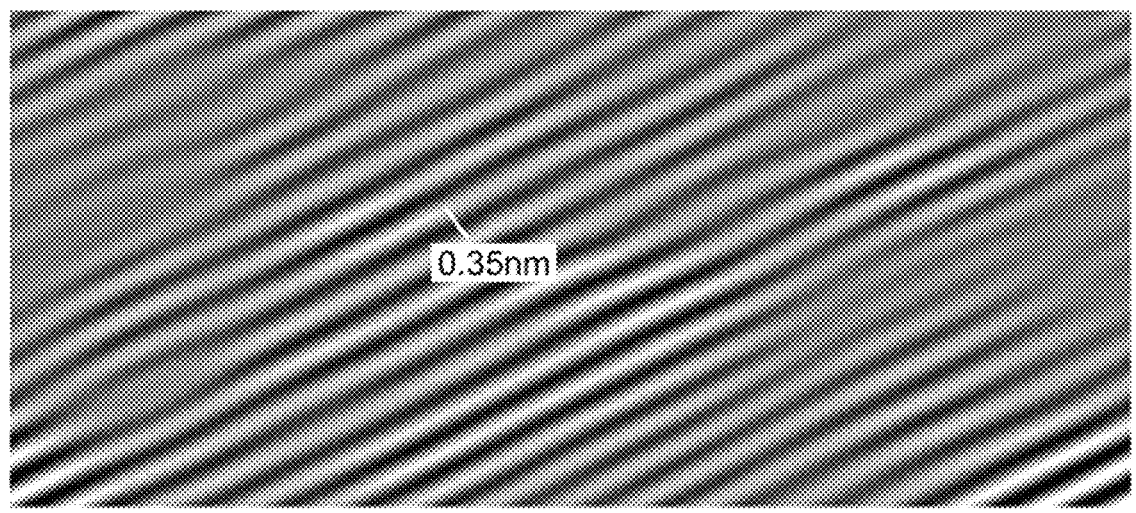
FIG. 2E is a graph depicting inverse fast Fourier transform (FFT) spectra image of an inventive 10% $g-C_3N_4@MoO_3/MgAl_2O_4$ nanocomposite.

Further, TEM images of g-$C_3N_4$@$MoO_3$/$MgAl_2O_4$ nanocomposite are shown in FIG. 2A. The TEM images showed the well dispersion of homogeneous spherical metal oxides nanoparticles with a size of about 9.4 nm on two-dimensional porous structure constructed with curled and wrinkled nanosheets and platelets of the g-$C_3N_4$. The corresponding SAED pattern, as shown in FIG. 2B, reveals diffraction spots with interplanar spacing of 0.245 nm, 0.19 nm, 0.155 nm, 0.127 nm, 0.12 nm due to (311, spinel), (411, $MoO_3$) and (511, spinel), (311, MgO), and (622, spinel) diffraction planes. The corresponding HRTEM, as shown in FIG. 2C, of the composite shows a plane spacing of 0.34 nm related to the (002) of CN, where 0.25 nm and 0.24 nm relates to (311) planes of spinel as well as (410) of $MoO_3$, and 0.32 nm relates to (210) plane of $MoO_3$, characterizing the heterostructure formation. The fast Fourier transform (FFT) and inverse fast Fourier transform (IFFT) measurements, depicted in FIGS. 2D-2E, show a 'd' value of 0.35 nm given to g-$C_3N_4$@$MoO_3$/$MgAl_2O_4$ nanocomposite, signifying the lattice spacing of (002), indicating the development of g-$C_3N_4$ structure.

According to the present disclosure, the cells were grown on RPMI-1640 medium supplemented with 10% inactivated fetal calf serum and 50 µg/ml gentamycin. The cells were maintained at 37° C. in a humidified atmosphere with 5% $CO_2$ and were sub-cultured two to three times a week.

For antitumor assays, the tumor cell lines were suspended in medium at concentration $5\times10^4$ cell/well in 96-well tissue culture plates (Corning®), followed by incubation for 24 hours. Furthermore, the tested compounds were added into 96-well plates (three replicates) to achieve ten concentrations for each compound. Six vehicle controls with media were run for each 96-well plate as a control. After incubating for 24 hours, the numbers of viable cells were determined by the 3-(4,5-dimethylthiazol-2-yl)-2,5-diphenyltetrazolium bromide (MTT) test. Moreover, the media was removed from the 96-well plate and replaced with 100 microliters (µL) of fresh culture RPMI 1640 medium without phenol red, followed by 10 µL of the 12 millimolar (mM) MTT stock solution (5 mg of MTT in 1 mL of PBS) to each well including the untreated controls. The 96-well plates were then incubated at 37° C. and 5% $CO_2$ for 4 hours. An 85 µL aliquot of the media was removed from the wells, and 50 µL of dimethyl sulfoxide (DMSO) was added to each well and mixed thoroughly with a pipette and incubated at 37° C. for 10 minutes. In addition, in order to determine the number of viable cells, optical density was measured at 590 nm with a microplate reader (SunRise, TECAN, Inc, USA). The percentage viability was calculated using the following expression, $$\left(\frac{ODt}{ODc}\right)\times 100\%$$

where 'ODt' is the mean optical density of wells treated with the tested sample and 'ODc' is the mean optical density of untreated cells. The relation between surviving cells and drug concentration is plotted to get the survival curve of each tumor cell line after treatment with the specified compound. The 50% inhibitory concentration ($IC_{50}$) required to cause toxic effects in 50% of intact cells was estimated from graphic plots of the dose-response curve for each concentration using GraphPad Prism software (San Diego, CA).

Figure 3:
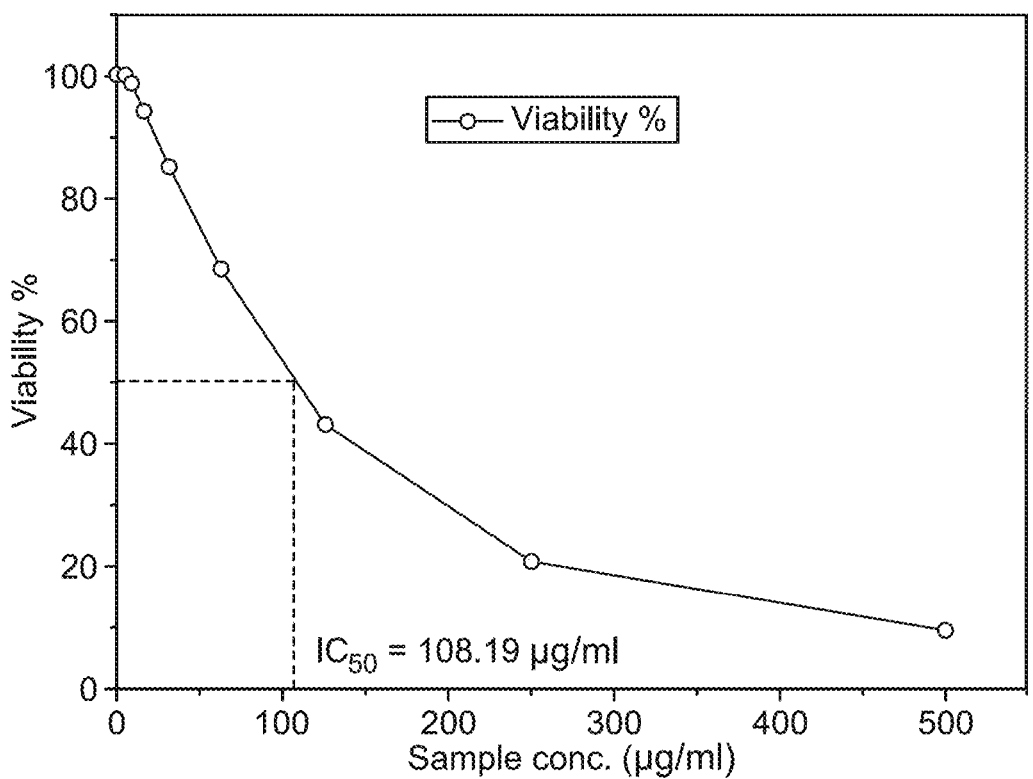
FIG. 3 is a graph depicting inhibitory activity of an inventive 10% $g-C_3N_4@MoO_3/MgAl_2O_4$ nanocomposite against MCF-7 cancer cell.

An in-vitro investigation was conducted for the g-$C_3N_4$@$MoO_3$/$MgAl_2O_4$ against the human hepatocellular carcinoma (HepG-2) and human breast carcinoma cell lines (MCF-7). A concentration range of 3.0 µg/mL to 500 µg/mL of the g-$C_3N_4$@$MoO_3$/$MgAl_2O_4$ nanocomposite was used. The obtained results against the MCF-7 cell line are illustrated in FIG. 3. The cell viability of the MCF-7 cell started declining with only 7.8 µg/mL g-$C_3N_4$@$MoO_3$/$MgAl_2O_4$ dose. The $IC_{50}$ was 108.19 µg/ml, and the maximum dose of about 500 µg/mL showed a 90.3% inhibition of the MCF-7 cancer cells.

Figure 4:
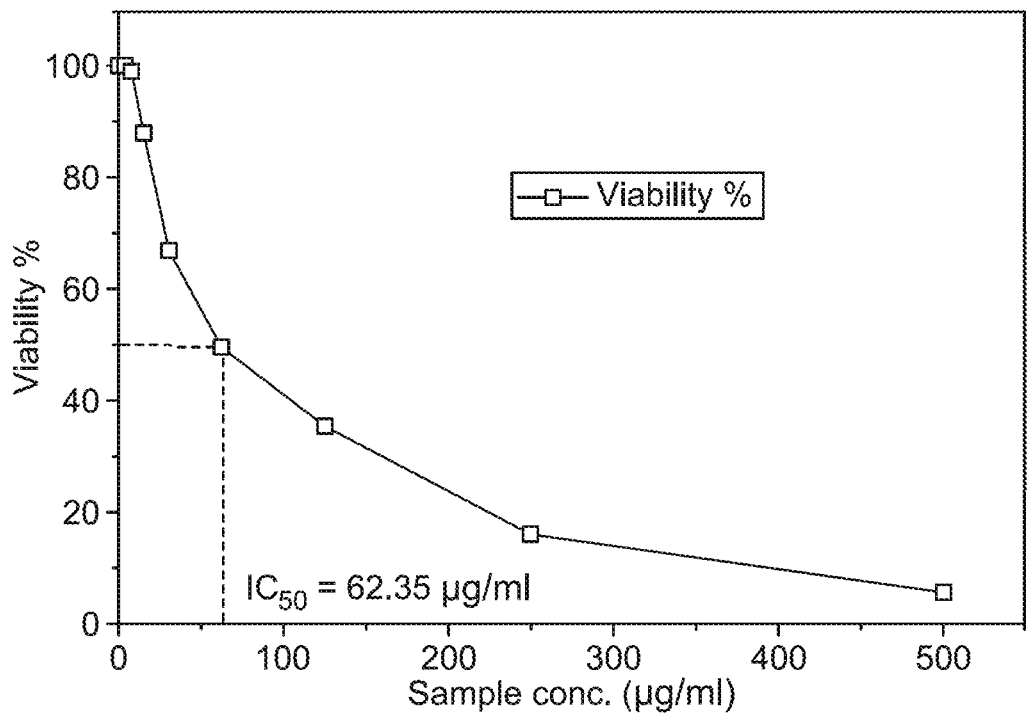
FIG. 4 is a graph depicting inhibitory activity of an inventive 10% $g-C_3N_4@MoO_3/MgAl_2O_4$ nanocomposite against HepG-2 cancer cell.

Furthermore, the exact concentration range at 3.0 µg/mL to 500 µg/mL of the g-$C_3N_4$@$MoO_3$/$MgAl_2O_4$ nanocomposite was applied against the HepG-2 cell line, and the obtained results against the HepG-2 cell line are illustrated in FIG. 4. The cell viability of the HepG-2 cell started declining with only 7.8 µg/mL g-$C_3N_4$@$MoO_3$/$MgAl_2O_4$ dose. The $IC_{50}$ was 62.35 µg/mL, and the maximum dose of about 500 µg/mL showed a 94.1% inhibition of the HepG-2 cancer cells.

The viability of MCF-7 cells may be reduced by 50, 40, 33, or 25% with the use of 0 to 50 µg/mL of the nanocomposite, while the viability of MCF-7 cells may be reduced another 40, 33, 25, or 20% with the use of an additional 50 g/mL of the nanocomposite or by 15, 10, 7.5, or 5% with the use of an additional 100 µg/mL of the nanocomposite or by 10, 7.5, 6.25, 5, 4, or 3.33% with the use of an additional 150 µg/mL of the nanocomposite. By increasing the concentration from 250 µg/mL to 500 µg/L of the nanocomposite, the viability of MCF-7 cells may be reduced by 15, 12.5, 10, 9, 8, 7.5, 7, 6, or 5%.

The viability of HepG-2 cells may be reduced by 40, 33, 25, 20, or 15% with the use of 0 to 50 µg/mL of the nanocomposite, while the viability of HepG-2 cells may be reduced by 25, 20, 15, 10, 7.5, or 5% with the use of an additional 50 µg/mL of the nanocomposite or by 15, 10, 7.5, or 5% with the use of an further additional 50 µg/mL of the nanocomposite or by 10, 7.5, 6.25, 5, 4, or 3.33% with the use of yet another additional 50 µg/mL of the nanocomposite. By increasing the concentration from 250 µg/mL to 500 µg/L of the nanocomposite, the viability of HepG-2 cells may be reduced by 10, 9, 8, 7.5, 7, 6, or 5%.

Numerous modifications and variations of the present disclosure are possible in light of the above teachings. It is therefore to be understood that within the scope of the appended claims, the invention may be practiced otherwise than as specifically described herein.

The invention claimed is:

1. A method of inhibiting cancer cell viability, the method comprising:
    contacting cancer cells and a nanocomposite comprising graphitic $C_3N_4$, $MoO_3$, and $MgAl_2O_4$ in a mass relationship to each other in a range of from 5 to 15:2 to 7:75 to 95, the nanocomposite being at a concentration in a range of from 25.0 to 500 µg/mL, thereby inhibiting the growth of the cancer cells by at least 85%.

2. The method of claim 1, wherein the average pore distribution of the nanocomposite is unimodal, and
    wherein a BET specific surface area of the nanocomposite is in a range of from 8 to 12 $m^2$/g, and/or
    wherein an average pore diameter of the nanocomposite, according to the BJH measurement method, is in a range of from 5 to 15 nm, and/or
    wherein an average pore volume of the nanocomposite, according to the BJH measurement method, is in a range of from 0.01 to 0.5 $cm^3$/g.

3. The method of claim 1, wherein the nanocomposite has a (311) spinel interplanar spacing in a range of from 0.205 to 0.285 nm, (411) $MoO_3$ interplanar spacing in a range of from 0.150 to 0.230 nm, (511) spinel interplanar spacing in a range of from 0.115 to 0.195 nm, (311) MgO interplanar spacing in a range of from 0.087 to 0.167 nm, (622) spinel interplanar spacing in a range of from 0.080 to 0.160 nm, according to selected area diffraction.

4. The method of claim 1, wherein the mass relationship of the nanocomposite is in a range of from 9 to 11:4 to 6:84 to 86, wherein the nanocomposite has a (311) spinel interplanar spacing of 0.245±2% nm, (411) $MoO_3$ interplanar spacing of 0.19±2% nm, (511) spinel interplanar spacing of 0.155±2% nm, (311) MgO interplanar spacing of 0.127±2% nm, (622) spinel interplanar spacing of 0.12±2% nm, according to selected area diffraction, wherein an XRD spectrum of the nanocomposite under Cu-filtered CuKα radiation (1.5418 Å) powered at 45 kV and 10 mA has 2θ peaks of an $MoO_3$ hexagonal phase at 18.7±1, 28.7±1, 33.0±1, 33.8±1, 36.8±1, and 42.8±1°, an $MgAl_2O_4$ spinel phase at 19.3±1, 36.8±1, 44.6±1, 59.3±1, and 65.01±1°, an MgO cubic phase at 42.8±1, 62.2±1, and 74.6±1°, $g-C_3N_4$-related diffractions at 27.8±1, 36.8±1, 44.6±1, and 59.3±1°, and wherein no more than 1% relative intensity $Al_2O_3$ is detected in the XRD spectrum.

5. The method of claim 1, wherein the cancer cells are HepG-2 human hepatocellular carcinoma cells and the concentration of the nanocomposite in the contacting is in a range of from 40 to 200 µg/mL, or wherein the cancer cells are MCF-7 human breast carcinoma cancer cells and the concentration of the nanocomposite is in a range of from 75 to 350 µg/mL.

6. The method of claim 1, wherein the nanocomposite comprises no $MoS_2$.

7. The method of claim 1, wherein the nanocomposite comprises no sulfide.

8. The method of claim 1, wherein the nanocomposite comprises no chitosan and no cellulose or modified cellulose.

9. The method of claim 1, wherein the nanocomposite comprises less than 1 wt. % Co, relative to total nanocomposite weight.

10. The method of claim 1, wherein the nanocomposite comprises no added Co, and/or wherein the method employs no folic acid and no rubicin drug.

11. The method of claim 1, wherein the nanocomposite comprises no more than 1 wt. % potassium.

12. The method of claim 1, wherein the nanocomposite comprises no more than 1 wt. % iron.

13. The method of claim 1, wherein the nanocomposite comprises no more than 1 wt. % zinc.

14. The method of claim 1, wherein the nanocomposite comprises no more than 1 wt. % carbonaceous material besides the graphitic carbon nitride, and/or wherein the method employs no electrochemiluminescence.

15. The method of claim 1, wherein the nanocomposite has a structure comprising a dispersion of homogeneous spherical metal oxides nanoparticles on a two-dimensional porous structure comprising curled and wrinkled nanosheets and platelets of the $g-C_3N_4$.

16. The method of claim 1, wherein the nanocomposite comprises no photosensitizer capable of converting oxygen molecules into singlet oxygen.

17. The method of claim 1, wherein the nanocomposite comprises no more than 1 wt. % of iron, cobalt, nickel, and/or copper.

18. The method of claim 1, wherein the nanocomposite comprises no more than 0.5 wt. % of elemental metal.

19. The method of claim 1, wherein the nanocomposite comprises no more than 0.0001 wt. % methylene blue or protoporphyrin.

20. The method of claim 1, wherein the nanocomposite comprises no more than 1 wt. % $Ba(OH)_2$.

\* \* \* \* \*